US012318632B2

(12) United States Patent
Garonna et al.

(10) Patent No.: US 12,318,632 B2
(45) Date of Patent: Jun. 3, 2025

(54) HEART ARRHYTHMIA NON-INVASIVE TREATMENT DEVICE AND METHOD

(71) Applicant: EBAMed SA, Geneva (CH)

(72) Inventors: Adriano Garonna, Geneva (CH); Giovanni Leo, Cologny (CH)

(73) Assignee: EBAMed SA, Geneva (CH)

( * ) Notice: Subject to any disclaimer, the term of this patent is extended or adjusted under 35 U.S.C. 154(b) by 0 days.

(21) Appl. No.: 18/628,649

(22) Filed: Apr. 5, 2024

(65) Prior Publication Data

US 2024/0269483 A1    Aug. 15, 2024

Related U.S. Application Data

(63) Continuation of application No. 17/717,310, filed on Apr. 11, 2022, now Pat. No. 11,951,327, which is a (Continued)

(30) Foreign Application Priority Data

Nov. 16, 2017    (EP) ..................................... 17202164

(51) Int. Cl.
*A61B 6/00*    (2024.01)
*A61N 5/10*    (2006.01)
*G16H 40/60*    (2018.01)

(52) U.S. Cl.
CPC ......... *A61N 5/1037* (2013.01); *A61N 5/1049* (2013.01); *A61N 5/1068* (2013.01); (Continued)

(58) Field of Classification Search
None
See application file for complete search history.

(56) References Cited

U.S. PATENT DOCUMENTS 3,399,302 A    8/1968    Carrell
3,923,060 A    12/1975    Ellinwood, Jr.
(Continued)

FOREIGN PATENT DOCUMENTS

BE    1024702 A1    5/2018
CA    2781536 A1    12/2012
(Continued)

OTHER PUBLICATIONS

U.S. Appl. No. 16/641,917 / U.S. Pat. No. 11,857,808, filed Feb. 25, 2020 / Jan. 2, 2024.
(Continued)

*Primary Examiner* — Hoon K Song
(74) *Attorney, Agent, or Firm* — Greenberg Traurig, LLP; Christopher C. Bolten; Robert D. Ward (57) ABSTRACT

The present invention relates to a heart tissue ablation device comprising a charged particle emitting system 1, a control system 2 for instructing the accelerator and beamline when to create the beam and what its required properties should be, a patient positioning and verification system, an ultrasound cardiac imaging system 3 performed on the patient, able to track the target movement, a computer program to determine and record the safe motion margins, the treatment plans for one or more motion phases and a computer program to regulate the control system 2 to load the correct irradiation plan according to the motion phase and if the position of the target is inside of the position margin, the irradiation is enabled and if the position of the target is outside of the position margin, the irradiation is disabled.

20 Claims, 1 Drawing Sheet

Related U.S. Application Data continuation of application No. 16/764,967, filed as application No. PCT/EP2018/081455 on Nov. 15, 2018, now Pat. No. 11,298,565.

(52) U.S. Cl.
CPC ..... *G16H 40/60* (2018.01); *A61N 2005/1058* (2013.01); *A61N 2005/1061* (2013.01); *A61N 2005/1087* (2013.01); *A61N 2005/1097* (2013.01)

(56) References Cited

U.S. PATENT DOCUMENTS

| | | |
|---|---|---|
| 5,538,494 A | 7/1996 | Matsuda |
| 5,590,657 A | 1/1997 | Cain et al. |
| 5,718,241 A | 2/1998 | Ben-Haim et al. |
| 5,764,723 A | 6/1998 | Weinberger et al. |
| 5,909,476 A | 6/1999 | Cheng et al. |
| 6,144,875 A | 11/2000 | Schweikard et al. |
| 6,443,896 B1 | 9/2002 | Detmer |
| 6,658,285 B2 | 12/2003 | Potse et al. |
| 6,710,362 B2 | 3/2004 | Kraft et al. |
| 6,780,152 B2 | 8/2004 | Üstüner et al. |
| 6,863,653 B1 | 3/2005 | Zanelli et al. |
| 6,889,695 B2 | 5/2005 | Pankratov et al. |
| 7,260,426 B2 | 8/2007 | Schweikard et al. |
| 7,322,929 B2 | 1/2008 | Lovoi |
| 7,346,381 B2 | 3/2008 | Okerlund et al. |
| 7,565,190 B2 | 7/2009 | Okerlund et al. |
| 7,645,276 B2 | 1/2010 | Pankratov et al. |
| 7,853,313 B2 | 12/2010 | Thomson |
| 7,953,204 B2 | 5/2011 | Sumanaweera et al. |
| 8,278,633 B2 | 10/2012 | Nord et al. |
| 8,295,435 B2 | 10/2012 | Wang et al. |
| 8,295,906 B2 | 10/2012 | Saunders et al. |
| 8,348,846 B2 | 1/2013 | Günther et al. |
| 8,351,571 B2 | 1/2013 | Brinks et al. |
| 8,422,631 B2 | 4/2013 | Takahashi et al. |
| 8,488,910 B2 | 7/2013 | Ruijters |
| 8,784,290 B2 | 7/2014 | Sumanaweera et al. |
| 8,792,613 B2 | 7/2014 | Gardner et al. |
| 8,805,481 B2 | 8/2014 | Sumanaweera et al. |
| 8,824,757 B2 | 9/2014 | Kolthammer et al. |
| 9,014,424 B2 | 4/2015 | Berlinger et al. |
| 9,061,144 B2 | 6/2015 | Fujii et al. |
| 9,108,048 B2 | 8/2015 | Maurer, Jr. et al. |
| 9,205,279 B2 | 12/2015 | Sumanaweera et al. |
| 9,289,268 B2 | 3/2016 | Ramraj et al. |
| 9,320,916 B2 | 4/2016 | Sumanaweera et al. |
| 9,326,751 B2 | 5/2016 | Hastings |
| 9,504,853 B2 | 11/2016 | Sumanaweera et al. |
| 9,526,476 B2 | 12/2016 | Schwartz et al. |
| 9,750,957 B2 | 9/2017 | Fujii et al. |
| 9,789,339 B2 | 10/2017 | Moskvin et al. |
| 9,907,978 B2 | 3/2018 | Pankratov et al. |
| 9,962,562 B2 | 5/2018 | Fahrig et al. |
| 9,968,801 B2 | 5/2018 | Sumanaweera et al. |
| 10,029,121 B2 | 7/2018 | Li et al. |
| 10,159,446 B2 | 12/2018 | Dickerson |
| 10,166,406 B2 | 1/2019 | Nord et al. |
| 10,251,629 B2 | 4/2019 | Belt et al. |
| 10,265,543 B2 | 4/2019 | Bharat et al. |
| 10,286,228 B2 | 5/2019 | Bharat et al. |
| 10,315,049 B2 | 6/2019 | Gauthier et al. |
| 10,342,558 B2 | 7/2019 | Steckner et al. |
| 10,363,439 B2 | 7/2019 | Amaldi |
| 10,485,992 B2 | 11/2019 | Heese et al. |
| 10,500,418 B2 | 12/2019 | Filiberti et al. |
| 10,548,496 B2 | 2/2020 | Gijsbers et al. |
| 10,646,188 B2 | 5/2020 | Mostafavi et al. |
| 10,792,511 B2 | 10/2020 | Pankratov et al. |
| 10,974,069 B2 | 4/2021 | Maguire et al. |
| 11,097,127 B2 | 8/2021 | Sumanaweera et al. |
| 11,272,902 B2 | 3/2022 | Geelen et al. |
| 11,298,565 B2 | 4/2022 | Garonna et al. |
| 11,406,845 B2 | 8/2022 | Robinson et al. |
| 11,506,801 B2 | 11/2022 | Sauli et al. |
| 11,857,808 B2 | 1/2024 | Packer et al. |
| 2002/0072674 A1 | 6/2002 | Criton et al. |
| 2002/0095197 A1 | 7/2002 | Lardo et al. |
| 2004/0015075 A1 | 1/2004 | Kimchy et al. |
| 2004/0162596 A1 | 8/2004 | Altshuler et al. |
| 2004/0260142 A1 | 12/2004 | Lovoi |
| 2004/0267113 A1 | 12/2004 | Thomson |
| 2005/0171396 A1 | 8/2005 | Pankratov et al. |
| 2006/0039591 A1 | 2/2006 | Zettel et al. |
| 2006/0074292 A1 | 4/2006 | Thomson et al. |
| 2006/0224053 A1 | 10/2006 | Black et al. |
| 2006/0241443 A1 | 10/2006 | Whitmore et al. |
| 2006/0291621 A1 | 12/2006 | Yan et al. |
| 2007/0041499 A1 | 2/2007 | Lu et al. |
| 2008/0021300 A1 | 1/2008 | Allison |
| 2008/0023644 A1 | 1/2008 | Pedroni |
| 2008/0081982 A1 | 4/2008 | Simon et al. |
| 2008/0177279 A1 | 7/2008 | Sumanaweera et al. |
| 2008/0177280 A1 | 7/2008 | Adler et al. |
| 2008/0191142 A1 | 8/2008 | Pedroni |
| 2008/0221382 A1 | 9/2008 | Karshafian et al. |
| 2008/0317204 A1 | 12/2008 | Sumanaweera et al. |
| 2009/0074278 A1 | 3/2009 | Beaulieu et al. |
| 2009/0076373 A1 | 3/2009 | Maschke |
| 2009/0080610 A1 | 3/2009 | Sumanaweera et al. |
| 2009/0180589 A1 | 7/2009 | Wang et al. |
| 2009/0206269 A1 | 8/2009 | Kraft et al. |
| 2009/0234237 A1 | 9/2009 | Ross et al. |
| 2009/0238404 A1 | 9/2009 | Orderud et al. |
| 2009/0253102 A1 | 10/2009 | Porikli et al. |
| 2009/0257557 A1 | 10/2009 | Sumanaweera et al. |
| 2009/0306515 A1 | 12/2009 | Matsumura et al. |
| 2010/0016744 A1 | 1/2010 | Brost et al. |
| 2010/0016765 A1 | 1/2010 | Hall et al. |
| 2010/0137709 A1 | 6/2010 | Gardner et al. |
| 2010/0145358 A1 | 6/2010 | Maschke |
| 2010/0183120 A1 | 7/2010 | Nord et al. |
| 2010/0217139 A1 | 8/2010 | Pinter et al. |
| 2010/0239066 A1 | 9/2010 | Fahrig et al. |
| 2010/0266099 A1 | 10/2010 | Busch et al. |
| 2010/0282983 A1 | 11/2010 | Wright et al. |
| 2010/0301235 A1 | 12/2010 | Bert et al. |
| 2010/0317968 A1 | 12/2010 | Wright et al. |
| 2011/0038516 A1 | 2/2011 | Koehler et al. |
| 2011/0107270 A1 | 5/2011 | Wang et al. |
| 2011/0137158 A1 | 6/2011 | Sumanaweera et al. |
| 2011/0160566 A1 | 6/2011 | Petropoulos et al. |
| 2011/0166407 A1 | 7/2011 | Sumanaweera et al. |
| 2011/0166408 A1 | 7/2011 | Sumanaweera et al. |
| 2011/0185503 A1 | 8/2011 | Yan |
| 2011/0190629 A1 | 8/2011 | Guenther et al. |
| 2011/0218438 A1 | 9/2011 | Hsieh et al. |
| 2012/0004518 A1 | 1/2012 | D'Souza et al. |
| 2012/0014501 A1 | 1/2012 | Pelc et al. |
| 2012/0083645 A1 | 4/2012 | Sun et al. |
| 2012/0134233 A1 | 5/2012 | Lin et al. |
| 2012/0146641 A1 | 6/2012 | Wu et al. |
| 2012/0181428 A1 | 7/2012 | Bert et al. |
| 2012/0241635 A1 | 9/2012 | Luechtenborg et al. |
| 2012/0292534 A1 | 11/2012 | Geneser et al. |
| 2012/0316423 A1 | 12/2012 | Raleigh et al. |
| 2012/0323233 A1 | 12/2012 | Maguire et al. |
| 2013/0035682 A1 | 2/2013 | Weil |
| 2013/0053617 A1 | 2/2013 | Pu et al. |
| 2013/0079645 A1 | 3/2013 | Amirana et al. |
| 2013/0211482 A1 | 8/2013 | Piipponen |
| 2013/0237822 A1 | 9/2013 | Gross et al. |
| 2013/0336450 A1 | 12/2013 | Kyriakou et al. |
| 2014/0005463 A1 | 1/2014 | Jongen |
| 2014/0107390 A1 | 4/2014 | Brown et al. |
| 2014/0107435 A1 | 4/2014 | Sharf et al. |
| 2014/0316247 A1 | 10/2014 | Hwang et al. |
| 2014/0343401 A1 | 11/2014 | Huber et al. |
| 2015/0004561 A1 | 1/2015 | Koehler |
| 2015/0080634 A1 | 3/2015 | Huber et al. |
| 2015/0092907 A1 | 4/2015 | Dong et al. |

(56) References Cited

U.S. PATENT DOCUMENTS

| | | |
|---|---|---|
| 2015/0112197 A1 | 4/2015 | Bharat |
| 2015/0146955 A1 | 5/2015 | Dong et al. |
| 2015/0150643 A1 | 6/2015 | Trayanova et al. |
| 2015/0173698 A1* | 6/2015 | Sakaguchi ............ A61B 8/466 378/62 |
| 2015/0182760 A1 | 7/2015 | Raleigh et al. |
| 2015/0209599 A1 | 7/2015 | Schlosser et al. |
| 2015/0290472 A1 | 10/2015 | Maguire et al. |
| 2015/0331118 A1 | 11/2015 | Iltis |
| 2015/0343238 A1 | 12/2015 | Balakin |
| 2015/0371420 A1 | 12/2015 | Yerushalmy et al. |
| 2016/0000409 A1 | 1/2016 | Bruder et al. |
| 2016/0035108 A1 | 2/2016 | Yu et al. |
| 2016/0058368 A1 | 3/2016 | Swaminathan et al. |
| 2016/0074674 A1 | 3/2016 | Kohli et al. |
| 2016/0082284 A1 | 3/2016 | Ooga et al. |
| 2016/0114189 A1 | 4/2016 | Mihailescu |
| 2016/0117850 A1 | 4/2016 | Jin et al. |
| 2016/0121142 A1 | 5/2016 | Zhang et al. |
| 2016/0125625 A1 | 5/2016 | Kim et al. |
| 2016/0184610 A1 | 6/2016 | Porikli |
| 2016/0324499 A1 | 11/2016 | Sen Sharma et al. |
| 2016/0331262 A1 | 11/2016 | Kuck et al. |
| 2016/0338676 A1 | 11/2016 | Berger et al. |
| 2016/0339271 A1 | 11/2016 | Bach et al. |
| 2016/0371862 A1 | 12/2016 | Silver et al. |
| 2017/0014642 A1 | 1/2017 | An et al. |
| 2017/0014645 A1 | 1/2017 | Foo et al. |
| 2017/0042515 A1 | 2/2017 | Schwartz et al. |
| 2017/0080253 A1 | 3/2017 | Clayton |
| 2017/0095197 A1 | 4/2017 | Kleiner et al. |
| 2017/0106208 A1 | 4/2017 | Gauthier et al. |
| 2017/0128744 A1 | 5/2017 | Adler et al. |
| 2017/0203123 A1 | 7/2017 | Requardt et al. |
| 2018/0153467 A1 | 6/2018 | Lichtenstein et al. |
| 2018/0185671 A1 | 7/2018 | Filiberti et al. |
| 2018/0214713 A1 | 8/2018 | Dehghan Marvast et al. |
| 2018/0243584 A1 | 8/2018 | Nord et al. |
| 2018/0252825 A1 | 9/2018 | Benlloch Baviera et al. |
| 2018/0318606 A1 | 11/2018 | Robinson et al. |
| 2019/0099621 A1 | 4/2019 | Koehl et al. |
| 2019/0164288 A1 | 5/2019 | Wang et al. |
| 2019/0344098 A1 | 11/2019 | Maguire et al. |
| 2019/0351254 A1 | 11/2019 | Sumanaweera et al. |
| 2019/0380670 A1 | 12/2019 | Hofmann et al. |
| 2020/0016429 A1 | 1/2020 | Maguire et al. |
| 2020/0090345 A1 | 3/2020 | Krebs et al. |
| 2020/0113546 A1 | 4/2020 | Madore et al. |
| 2020/0151921 A1 | 5/2020 | Schildkraut |
| 2020/0179722 A1* | 6/2020 | Packer ................. A61N 5/1037 |
| 2021/0012544 A1 | 1/2021 | Lee et al. |
| 2021/0015454 A1 | 1/2021 | Puleo et al. |
| 2021/0065414 A1 | 3/2021 | Do |
| 2021/0093897 A1* | 4/2021 | Zadicario ............ A61B 5/0035 |
| 2021/0137384 A1* | 5/2021 | Robinson ................. G06T 7/10 |
| 2022/0183657 A1 | 6/2022 | McLaughlin et al. |
| 2022/0386987 A1 | 12/2022 | Camps et al. |

FOREIGN PATENT DOCUMENTS

| | | |
|---|---|---|
| CN | 1672651 A | 9/2005 |
| CN | 101268467 A | 9/2008 |
| CN | 101600473 A | 12/2009 |
| CN | 102119586 A | 7/2011 |
| CN | 102196768 A | 9/2011 |
| CN | 102510735 A | 6/2012 |
| CN | 102781359 A | 11/2012 |
| CN | 103180015 A | 6/2013 |
| CN | 103279929 A | 9/2013 |
| CN | 104349817 A | 2/2015 |
| CN | 105813691 A | 7/2016 |
| CN | 106291656 A | 1/2017 |
| CN | 107730455 A | 2/2018 |
| CN | 108022272 A | 5/2018 |
| CN | 111223156 A | 6/2020 |
| DE | 102013102920 A1 | 9/2014 |
| DE | 102013112573 A1 | 6/2015 |
| DE | 102014217966 A1 | 3/2016 |
| EP | 0327459 B1 | 9/1992 |
| EP | 2140913 A1 | 1/2010 |
| EP | 2290406 A2 | 3/2011 |
| EP | 2523623 A1 | 11/2012 |
| EP | 2942081 A1 | 11/2015 |
| EP | 2950119 A1 | 12/2015 |
| EP | 3036978 A1 | 6/2016 |
| FR | 2930995 A1 | 11/2009 |
| FR | 3058249 A3 | 5/2018 |
| JP | 2005095640 A | 4/2005 |
| JP | 2006113061 A | 4/2006 |
| JP | 2007047066 A | 2/2007 |
| JP | 2007526010 A | 9/2007 |
| JP | 2010540050 A | 12/2010 |
| JP | 2012533364 A | 12/2012 |
| JP | 2016214438 A | 12/2016 |
| KR | 20110040164 A | 4/2011 |
| WO | WO-0126569 A1 | 4/2001 |
| WO | WO-2008086434 A2 | 7/2008 |
| WO | WO-2009111783 A2 | 9/2009 |
| WO | WO-2011012154 A1 | 2/2011 |
| WO | WO-2011021410 A1 | 2/2011 |
| WO | WO-2012104416 A1 | 8/2012 |
| WO | WO-2012152938 A2 | 11/2012 |
| WO | WO-2012154219 A2 | 11/2012 |
| WO | WO-2013034709 A1 | 3/2013 |
| WO | WO-2013129811 A1 | 9/2013 |
| WO | WO-2013179221 A1 | 12/2013 |
| WO | WO-2015025203 A1 | 2/2015 |
| WO | WO-2015040225 A1 | 3/2015 |
| WO | WO-2015053737 A1 | 4/2015 |
| WO | WO-2016193929 A2 | 12/2016 |
| WO | WO-2017066358 A1 | 4/2017 |
| WO | WO-2017078757 A1 | 5/2017 |
| WO | WO-2017156113 A1 | 9/2017 |
| WO | WO-2019017752 A1 | 1/2019 |
| WO | WO-2019096943 A1 | 5/2019 |
| WO | WO-2020033355 A1 | 2/2020 |
| WO | WO-2020075106 A2 | 4/2020 |
| WO | WO-2020142397 A1 | 7/2020 |
| WO | WO-2020212573 A1 | 10/2020 |
| WO | WO-2021094824 A1 | 5/2021 |
| WO | WO-2022136925 A1 | 6/2022 |

OTHER PUBLICATIONS

U.S. Appl. No. 16/764,967 / U.S. Pat. No. 11,298,565, filed May 18, 2020 / Apr. 12, 2022.

U.S. Appl. No. 17/284,101 / U.S. Pat. No. 11,506,801, filed Apr. 9, 2021 / Nov. 22, 2022.

U.S. Appl. No. 17/717,310 / U.S. Pat. No. 11,951,327, filed Apr. 11, 2022 / Apr. 9, 2024.

U.S. Appl. No. 17/776,004, filed May 11, 2022.

U.S. Appl. No. 17/897,771, filed Aug. 29, 2022.

U.S. Appl. No. 17/992,042, filed Nov. 22, 2022.

U.S. Appl. No. 18/269,351, filed Jun. 23, 2023.

U.S. Appl. No. 18/542,354, filed Dec. 15, 2023.

U.S. Appl. No. 29/927,660, filed Feb. 5, 2024.

U.S. Appl. No. 18/597,839, filed Mar. 6, 2024.

Achenbach S., et al., "Noninvasive Coronary Angiography by Retrospectively ECG-Gated Multislice Spiral CT," Circulation, 102(23):2823-2828 (Dec. 2000).

Asirvatham S.J., "Advances in Catheter Ablation: A Burning Trail!," Indian Heart Journal, 2011, pp. 379-385.

Bai S., et al., "An Empirical Evaluation of Generic Convolutional and Recurrent Networks for Sequence Modeling," arXiv Prepr. arXiv:1803.01271v2, Apr. 19, 2018, 14 Pages.

Baker, et al., "Prostate Displacement During Transabdominal Ultrasound Image-Guided Radiotherapy Assessed by Real-Time Four-dimensional Transperineal Monitoring," Acta Oncologica, 2015, vol. 54, No. 9, pp. 1508-1514.

(56) References Cited

OTHER PUBLICATIONS

Beddar A.S., et al., "Correlation Between Internal Fiducial Tumor Motion and External Marker Motion for Liver Tumors Imaged With 4D-CT," International Journal of Radiation Oncology, Biology, Physics, vol. 67(2):630-638 (Feb. 2007).
Beltrame P., et al., "Construction and Tests of Demonstrator Modules for a 3-D Axial PET System for Brain or Small Animal Imaging," Nuclear Instruments and Methods in Physics Research A, 2011, vol. 636, pp. S226-S230, Available Online May 5, 2010.
Bert C., et al., "Motion in Radiotherapy: Particle Therapy," Physics in Medicine and Biology, 2011, vol. 56, pp. R113-R44.
Bertholet, et al., "Real-Time Intrafraction Motion Monitoring in External Beam Radiotherapy," Physics in Medicine, 2019, vol. 64, No. 15.
Blanck O., et al., "Dose-Escalation Study for Cardiac Radiosurgery in a Porcine Model," Int J Radiat Oncol Biol Phys., vol. 89:590-598 (Dec. 2014).
Blanck, "Radiosurgery for Ventricular Tachycardia: Preclinical and Clinical Evidence and Study Design for a German Multi-Center Multi-Platform Feasibility Trial (Raventa)," Clinical Research in Cardiology, 09:1319-1332 (Nov. 2020).
Boas F.E., et al., "Evaluation of Two Iterative Techniques for Reducing Metal Artifacts in Computed Tomography," Radiology, Jun. 2011, vol. 259, No. 3, pp. 894-902.
Bode F., et al., "Pulmonary Vein Isolation by Radiosurgery: Implications for Non-Invasive Treatment of Atrial Fibrillation," Europace, vol. 17:1868-1874 (Mar. 2015).
Braem A., et al., "AX-PET: A Novel PET Detector Concept with Full 3D Reconstruction," Nuclear Instruments and Methods in Physics Research A, 2009, vol. 610, pp. 192-195, Available Online May 29, 2009.
Calkins H., et al., "2012 HRS/EHRA/ECAS Expert Consensus Statement on Catheter and Surgical Ablation of Atrial Fibrillation: Recommendations for Patient Selection Procedural Techniques, Patient Management and Follow-Up, Definitions, Endpoints, and Research Trial Design," Heart Rhythm, 2012, vol. 9(4):632-696(e21) (Apr. 2012).
Cappato R., et al., "Updated Worldwide Survey on the Methods, Efficacy, and Safety of Catheter Ablation for Human Atrial Fibrillation," Circulation: Arrhythmia and Electrophysiology, 2010, vol. 3, pp. 32-38, DOI: 10.1161/CIRCEP.109.859116.
Casella C., et al., "A High Resolution TOF-PET Concept With Axial Geometry and Digital SiPM Readout," Nuclear Instruments and Methods in Physics Research A, 2014, vol. 736, pp. 161-168.
Chaudhri, et al., "SU-E-T-334: Clinical Implementation of Gating and Dose Verification with Scanned Ion Beams at HIT," Medical Physics, The American Association of Physicists in Medicine, 39(Issue 6—Part 15):3780-3781 (Jun. 2012).
Che, et al., "Ultrasound Registration: A Review," Methods, 115:128-143 (Feb. 2017).
Constantinescu A., et al., "Catheter-Free Ablation of Atrial Fibrillation: Further Planning Studies in Patient Data Using a Scanned Carbon Ion Beam for Pulmonary Vein Isolation, MP04-02," Hearth Rhythm, May 2014, vol. 11 No. 5, Supplement.
Constantinescu A., et al., "Planning Studies for Non-Invasive Isolation of the Pulmonary Veins with a Scanned Carbon Ion Beam," Heart Rhythm, 2013, vol. 10, p. S33.
Constantinescu A., et al., "Treatment Planning Studies in Patient Data with Scanned Carbon Ion Beams for Catheter-Free Ablation of Atrial Fibrillation," Journal of Cardiovascular Electrophysiology, 2016, vol. 27, No. 3, pp. 335-344.
De Luca, et al., "The 2014 Liver Ultrasound Tracking Benchmark," Physics in Medicine & Biology, 60(14):5571 (Jul. 2015).
De Vries T., et al. "Improved Regularization of Convolutional Neural Networks with Cutout," University of Guelph, Canadian Institute for Advanced Research and Vector Institute, Nov. 29, 2017, 08 Pages.
Degiovanni A., et al., "Design of a Fast-Cycling High-Gradient Rotating Linac for Protontherapy," Proceedings of IPAC, Shanghai, China THPWA008, 2013, pp. 3642-3644.
Deisher A., et al., "Catheter-Free Ablation With External Photon Radiation: Treatment Planning, Delivery Considerations, and Correlation of Effects With Delivered Dose," Heart Rhythm, May 2015, vol. 12, No. 5, Supplement.
Del Carpio Munoz F., et al., "Three-Dimensional Mapping of Cardiac Arrhythmias: What do the Colors Really Mean?," Circulation Arrhythmia and Electrophysiology, Dec. 2010, vol. 3, No. 6, pp. e6-e11.
Deneke T., et al., "Silent Cerebral Events/Lesions Related to Atrial Fibrillation Ablation: A Clinical Review," Journal of Cardiovascular Electrophysiology, 2015, vol. 26, pp. 455-463, DOI: 10.1111/jce.12608.
Depuydt, et al., "Treating Patients With Real-Time Tumor Tracking Using the Vero Gimbaled Linac System: Implementation and First Review," Radiotherapy and Oncology, 2014, vol. 112, No. 3, pp. 343-351.
Dickfeld T., et al., "MRI-Guided Ventricular Tachycardia Ablation: Integration of Late Gadolinium-Enhanced 3D Scar in Patients with Implantable Cardioverter-Defibrillators," Circulation Arrhythmia and Electrophysiology, 2011, vol. 4, pp. 172-184. DOI: 10.1161/CIRCEP.110.958744.
Dieterich S., et al., "Respiratory Motion Management for External Beam Radiotherapy," Practical Radiation Oncology Physics, Elsevier Inc., 2016, pp. 252-263.
Dinov B., et al., "Early Referral for Ablation of Scar-Related Ventricular Tachycardia is Associated with Improved Acute and Long-Term Outcomes: Results from the Heart Center of Leipzig Ventricular Tachycardia Registry," Circulation Arrhythmia and Electrophysiology, 2014, vol. 7, pp. 1144-1151, DOI: 10.1161/CIRCEP.114.001953.
Extended European Search Report for European Application No. 18851934.2, mailed Sep. 15, 2021, 13 Pages.
Fayad, et al., "Technical Note: Correlation of Respiratory Motion Between External Patient Surface and Internal Anatomical Landmarks," Medical Physics, 38(6):3157-3164 (Jun. 2011).
Fiorito A.M., et al., "Detection of Cardiac Events in Echocardiography Using 3D Convolutional Recurrent Neural Networks", 2018 IEEE International Ultrasonics Symposium (IUS), Oct. 22, 2018, 04 Pages, Doi:10.1109/ULTSYM.2018.8580137, XP033523144.
Fishbein M.C., et al., Early Phase Acute Myocardial Infarct Size Quantification: Validation of the Triphenyl Tetrazolium Chloride Tissue Enzyme Staining Technique, American Heart Journal, 1981, vol. 101, pp. 593-600.
Fontanarosa, et al., "Review of Ultrasound Image Guidance in External Beam Radiotherapy: I. Treatment Planning and Inter-Fraction Motion Management," Physics in Medicine & Biology, 60(3):R77-R114 (Jan. 2015).
Franceschi F., et al., "Histopathological Effects and Evolution of Transvenous β-Radiation Applications in Right and Left Atria: An Animal Study," Europace, 2012, vol. 14, pp. 745-751, DOI: 10.1093/europace/eur351.
Ge J., et al., "Planning 4-Dimensional Computed Tomography (4DCT) Cannot Adequately Represent Daily Intrafractional Motion of Abdominal Tumors," International Journal of Radiation Oncology, Biology, Physics, vol. 85(4):999-1005 (Mar. 2013).
Gerstenfeld E.P., "Recurrent Ventricular Tachycardia after Catheter Ablation in Post-Infarct Cardiomyopathy: "Failure" of Ablation or Progression of the Substrate?," Journal of the American College of Cardiology, 2013, vol. 61, pp. 74-76, DOI: 10.1016/j.jacc.2012.07.057.
Graeff C., et al., "A 4D-Optimization Concept for Scanned Ion Beam Therapy," Radiotherapy and Oncology, Available Online Oct. 31, 2013, vol. 109, pp. 419-424.
Graeff C., et al., "Motion Mitigation in Intensity Modulated Particle Therapy by Internal Target Volumes Covering Range Changes," Medical Physics, 2012, vol. 39, pp. 6004-6013.
Graeff, et al., "Noninvasive Cardiac Arrhythmia Ablation With Particle Beams," Medical Physics, vol. 45, No. 11 (Nov. 2018).
Grimm J., et al., "Dose Tolerance Limits and Dose Volume Histogram Evaluation for Stereotactic Body Radiotherapy," Journal of Applied Clinical Medical Physics, vol. 12(2): 267-292 (Jan. 2011).

(56) References Cited

OTHER PUBLICATIONS

Guerra P.G., et al., "Beta-Radiation for the Creation of Linear Lesions in the Canine Atrium," Circulation, 2004, vol. 110, pp. 911-914, DOI: 10.1161/01.CIR.0000139865.39885.03.

Haberer T., et al., "Magnetic Scanning System for Heavy ion Therapy," Nuclear Instruments and Methods A, 1993, vol. 330, pp. 296-305.

Hartman J., et al., "Dosimetric Feasibility of Intensity Modulated Proton Therapy in a Transverse Magnetic Field of 1.5 T," Physics in Medicine and Biology, 2015, vol. 60, pp. 5955-5969.

Hoogeman, et al., "Clinical Accuracy of the Respiratory Tumor Tracking System of the Cyberknife: Assessment by Analysis of Log Files," International Journal of Radiation Oncology, Biology, Physics, 2009, vol. 74, No. 1, pp. 297-303, DOI: 10.1016/j.ijrobp.2008.12.041, XP026037471.

Iguchi T., et al., "Development of Compact Compton Gamma Camera for Non-Destructive Detection and Location of Hidden Explosives with Neutron Induced Prompt Gamma-Ray Imaging," Nuclear Science Symposium Conference Record, IEE Wyndham EI Conquistador Resort, Puerto Rico, Piscataway, NJ, USA, IEEE, Oct. 23-29, 2005, vol. 2, pp. 735-739, DOI:10.1109/NSSMIC.2005.1596362, ISBN 978-0-7803-9221-2, XP010895599.

International Search Report & Written Opinion dated Dec. 11, 2023 in Int'l PCT Patent Appl. Serial No. PCT/IB2023/058539 (0710).

International Search Report and Written Opinion for International Application No. PCT/EP2018/081455, mailed Feb. 12, 2019, 13 Pages.

International Search Report and Written Opinion for International Application No. PCT/IB2019/058638, mailed Jun. 25, 2020, 17 Pages.

International Search Report and Written Opinion for International Application No. PCT/IB2020/000930, mailed Apr. 9, 2021, 11 Pages.

International Search Report and Written Opinion for International Application No. PCT/IB2021/000922, mailed Apr. 19, 2022, 15 Pages.

International Search Report and Written Opinion for International Application No. PCT/US2018/049114, mailed Nov. 21, 2018, 09 Pages.

Ipsen, et al., "Radiotherapy Beyond Cancer: Target Localization in Real-time MRI and Treatment Planning for Cardiac Radiosurgery," Medical Physics, vol. 41(12):120702_1-120702_8 (Dec. 2014).

Ipsen, et al., "Target Tracking Accuracy and Latency With Different 4D Ultrasound Systems—A Robotic Phantom Study," Current Directions in Biomedical Engineering, 6(1):20200038 (Sep. 2020).

Ipsen, S., "See What You Treat: 4d Ultrasound Imaging for Real Time Motion Compensation in the Liver," PhD Thesis University of Luebeck, pp. 1-142 (Nov. 2019).

Kachelriess M., et al., "ECG-Correlated Image Reconstruction from Subsecond Multi-Slice Spiral CT Scans of the Heart," Medical Physics, 2000, vol. 27, pp. 1881-1902.

Keall et al., "The Management of respiratory motion in radiation on oncology report of AAPM Task Group 76$^{a)}$," Med. Phys., vol. 33(10):3874-3900 (Oct. 2006).

Keall P.J, et al., "The First Clinical Implementation of Electromagnetic Transponder-Guided MLC Tracking," Medical Physics, 2014, vol. 41: 020702.

Keall P.J., et al., "The First Clinical Treatment with Kilovoltage Intrafraction Monitoring (KIM): A Real-Time Image Guidance Method," Medical Physics, 2015, vol. 42, pp. 354-358.

Khalil, et al., "An Overview on Image Registration Techniques for Cardiac Diagnosis and Treatment," Cardiology Research and Practice, 2018, Article ID 1437125, 15 pages, https://doi.org/10.1155/2018/1437125.

Kincaid, et al., "Investigation of Gated Cone-Beam CT to Reduce Respiratory Motion Blurring," Medical Physics, 40(4):041717 (Apr. 2013).

Kingma D.P., et al., "Adam: A Method for Stochastic Optimization," Published as a Conference Paper at ICLR, arXiv: 1412.6980v8, Jul. 23, 2015, pp. 1-15.

Klein E.E., et al., "Task Group 142 report: Quality assurance of medical accelerators," Medical Physics, The American Association of Physicists in Medicine, Sep. 2009, vol. 36, No. 9, pp. 4197-4212, Published on Aug. 17, 2009.

Koike Y., et al., "Deep Learning-Based Metal Artifact Reduction Using Cycle-Consistent Adversarial Network for Intensity-Modulated Head and Neck Radiation Therapy Treatment Planning," Physica Medica, Sep. 7, 2020, vol. 78, pp. 8-14.

Krimmer J., et al., "Prompt-Gamma Monitoring in Hadrontherapy: A Review," Nuclear Instruments and Methods in Physics Research A, 2018, vol. 878, pp. 58-73, Available online Aug. 12, 2017.

Kumar S., et al., "Effect of Respiration on Catheter-Tissue Contact Force during Ablation of Atrial Arrhythmias," Heart Rhythm, vol. 9(7):1041-1047e1 (Jul. 2012).

Kuntz J., et al., "Fully Automated Intrinsic Respiratory and Cardiac Gating for Small Animal CT," Physics in Medicine and Biology, vol. 55:2069-2085 (Apr. 2010).

Lachaine, et al., "Intrafractional Prostate Motion Management With the Clarity Autoscan System," Medical Physics International Journal, 1(1):72-80 (2013).

Lehmann H.I., et al., "Atrioventricular Node Ablation in Langendorffperfused Porcine Hearts using Carbon Ion Particle Therapy: Methods and an in Vivo Feasibility Investigation for Catheter-Free Ablation of Cardiac Arrhythmias," Circulation Arrhythmia and Electrophysiology, Apr. 2015, vol. 8, pp. 429-438, DOI: 10.1161/ CIRCEP.114.002436.

Lehmann H.I., et al., "Biophysics of Tissue Ablation in Catheter-Free Ablation With Carbon Ion Beams," vol. 13:(5):AB29-05 S67 (May 1016).

Lehmann H.I., et al., "Delineation of Target Locations and Organs at Risk for Particle Beam Therapy: Atlas for Extracorporeal CT-Based Ablation of Cardiac Tissue," Heart Rhythm, May 2017 vol. 11, No. 5, Supplement.

Lehmann H.I., et al., "External Arrhythmia Ablation using Photon Beams: Ablation of the Atrioventricular Junction in an Intact Animal Model," Circulation: Arrhythmia and Electrophysiology, Apr. 2017, vol. 10, No. 4 (e004304).

Lehmann H.I., et al., "Feasibility Study on Cardiac Arrhythmia Ablation Using High-Energy Heavy Ion Beams," Nature, Scientific Reports, Dec. 20, 2016, vol. 6, No. 38895, 13 Pages, DOI: 10.1038/srep38895.

Lehmann H.I., et al., "In-Beam PET Verification of Catheter-Free Arrhythmia Ablation by Scanned Carbon-12 Ion Beam Irradiation," Circulation, 2015, vol. 132, Supplement. 3, p. A12443.

Li, et al., Comparative Quantitative Analysis of Robotic Ultrasound Image Calibration Methods, 2021 20th International Conference on Advanced Robotics (ICAR), IEEE, pp. 511-516.

Lin M.H., et al., "4D Patient Dose Reconstruction using Online Measured EPID Cine Images for Lung SBRT Treatment Validation," Medical Physics, 2012, vol. 39, pp. 5949-5958.

Lis M., et al., "A Modular Dose Delivery System for Treating Moving Targets With Scanned Ion Beams: Performance and Safety Characteristics, and Preliminary Tests," Physica Medica, 2020, vol. 76, pp. 307-316.

Luzhbin D., et al., "Model Image-Based Metal Artifact Reduction for Computed Tomography," Journal of Digital Imaging, 2020, vol. 33, pp. 71-82.

Maguire., et al., "First-In-Man Cardiac Radiosurgery for Atrial Arrhythmia," International Journal of Radiation Oncology, Biology, Physics, 96(2):E504-5 (Oct. 2016).

Maguire P., et al., "Cardiac Radiosurgery (CyberHeart) for Treatment of Arrhythmia: Physiologic and Histopathologic Correlation in the Porcine Model," Cureus, 3(8):(e32) (Aug. 2011).

Nakao M., et al., "Regularized Three-Dimensional Generative Adversarial Nets for Unsupervised Metal Artifact Reduction in Head and Neck CT Images," IEEE Access, Digital Object Identifier, Jun. 12, 2020, vol. 8, pp. 109453-109465.

Nankali, et al., "Geometric and Dosimetric Comparison of Four Intrafraction Motion Adaptation Strategies for Stereotactic Liver Radiotherapy," Physics in Medicine & Biology, 63(14):145010 (Jul. 2018).

(56) References Cited

OTHER PUBLICATIONS

Ng J., et al., "Mapping of Dominant Activation Directions in a Canine Rapid Atrial Pacing Model of Atrial Fibrillation," Heart Rhythm Session, May 12, 2017.
O'Shea, et al., "Review of Ultrasound Image Guidance in External Beam Radiotherapy Part II: Intra-Fraction Motion Management and Novel Applications," Physics in Medicine & Biology, 2016, vol. 61, No. 8, DOI: 10.1088/0031-9155/61/8/R90, XP020303407.
Okumura Y., et al., "Three-Dimensional Ultrasound for Image-Guided Mapping and Intervention: Methods, Quantitative Validation, and Clinical Feasibility of a Novel Multimodality Image Mapping System," Circulation Arrhythmia Electrophysiology, 2008, vol. 1, pp. 110-119, DOI: 10.1161/ CIRCEP.108.769935.
Ortega P.G., et al., "Noise Evaluation of Compton Camera Imaging for Proton Therapy," Physics in Medicine and Biology, Institute of Physics Publishing and Engineering in Medicine, Bristol, GB, Feb. 6, 2015, vol. 60, No. 5, pp. 1845-1863, DOI:10.1088/0031-9155/60/5/1845, ISSN 0031-9155.
Ortmaier T., et al., "Motion Estimation in Beating Heart Surgery," IEEE Transactions on Biomedical Engineering, 2005, vol. 52, pp. 1729-1740.
Pan J., et al., "A Real-Time QRS Detection Algorithm," IEEE Transactions on Biomedical Engineering, Mar. 1985, vol. BME-32, No. 3, pp. 230-236.
Partial Supplementary European Search Report for European Application No. 18851934.2, mailed Apr. 22, 2021, 11 Pages.
Perali I., et al., "Prompt Gamma Imaging of Proton Pencil Beams at Clinical Dose Rate," Institute of Physics and Engineering in Medicine, Physics in Medicine and Biology, Sep. 10, 2014, vol. 59, pp. 5849-5871.
Peulen H., et al., "Mid-Ventilation Based PTV Margins in Stereotactic Body Radiotherapy (SBRT): A Clinical Evaluation," Radiotherapy and Oncology, vol. 110:(3):511-516, DOI: 10.1016/j.radonc.2014.01.010 (Mar. 2014).
Pfanner F., et al. "Monitoring Cardiac Motion in CT using a Continuous Wave Radar Embedded in the Patient Table," Medical Physics, 2014, vol. 41: 081908.
Pfanner F., et al., "Monitoring internal organ motion with continuous wave radar in CT," Medical Physics, 2013, vol. 40: 091915.
Piersanti L., et al., Measurement of Charged Particle Yields from PMMA Irradiated by a 220 MeV/u (12)C Beam, Physics in Medicine and Biology, 2014, vol. 59, pp. 1857-1872.
Poon, et al., "Technical Note: Cardiac Synchronized Volumetric Modulated Arc Therapy for Stereotactic Arrhythmia Radioablation—Proof of Principle," Medical Physics, vol. 47(8):3567-3572 (Aug. 2020).
Poulsen P.R., et al., "A Method of Dose Reconstruction for Moving Targets Compatible with Dynamic Treatments," Medical Physics, vol. 39(10):6237-6246 (Oct. 2012).
Poulsen P.R., et al., "Kilovoltage Intrafraction Motion Monitoring and Target Dose Reconstruction for Stereotactic Volumetric Modulated Arc Therapy of Tumors in the Liver," Radiotherapy and Oncology, 2014, vol. 111, pp. 424-430.
Prall M., et al., "Ion Beam Tracking Using Ultrasound Motion Detection," Medical Physics, 41(4):041708-1-041708-5 (Apr. 2014).
Prall M., et al., "Treatment of Arrhythmias by External Charged Particle Beams: A Langendorff Feasibility Study," Biomedical Engineering-Biomedical Technology, Published Online on Feb. 19, 2015, vol. 60, No. 2, pp. 147-156.
Pérez-Castellano N., et al., "Pathological Effects of Pulmonary Vein Beta-Radiation in a Swine Model," Journal of Cardiovascular Electrophysiology, 2006, vol. 17, pp. 662-669, DOI: 10.1111/j.1540-8167.2006.00462.x.
Queiros, et al., "Fast Left Ventricle Tracking Using Localized Anatomical Affine Optical Flow," International Journal for Numerical Methods in Biomedical Engineering, 33(11):e2871 (Nov. 2017).
Raaymakers B.W., et al., "Integrating a 1.5 T MRI Scanner With A 6 MV Accelerator: Proof of Concept," Physics in Medicine and Biology, 54(12):N229-N37 (May 2009).
Ravkilde T., et al., "Time-Resolved Dose Distributions to Moving Targets During Volumetric Modulated Arc Therapy With and Without Dynamic MLC Tracking," Medical Physics, 2013, 40(11):111723-1-111723-8 (Nov. 2013).
Rettmann M.E., et al., "Analysis of Left Atrial Respiratory and Cardiac Motion for Cardiac Ablation Therapy," Medical Imaging 2015: Image-Guided Procedures, Robotic Interventions, and Modeling, 9415:651-656 ) Mar. 2015.
Rettmann M.E., et al., "Centerline Tracking for Quantification of Reverse Structural Remodeling of the Pulmonary Veins Following Cardiac Ablation Therapy," Academic Radiology, 19(11):1332-1344 (Nov. 2012).
Richter C., et al., "First Clinical Application of a Prompt Gamma Based in Vivo Proton Range Verification System," Radiotherapy and Oncology, vol. 118(2):232-237 (Feb. 2016).
Richter D., et al., "ECG-Based 4d-Dose Reconstruction of Cardiac Arrhythmia Ablation With Carbon Ion Beams: Application in a Porcine Model," Physics in Medicine and Biology, Aug. 4, 2017, vol. 62, No. 17, p. 6869.
Richter D., et al., "Four-Dimensional Patient Dose Reconstruction for Scanned Ion Beam Therapy of Moving Liver Tumors," International Journal of Radiation Oncology, Biology, Physics, 2014, vol. 89, pp. 175-181.
Richter D., et al., "Residual Motion Mitigation in Scanned Carbon Ion Beam Therapy of Liver Tumors Using Enlarged Pencil Beam Overlap," Radiotherapy and Oncology, vol. 113, pp. 290-295 (Nov. 2014).
Richter D., et al., "Upgrade and Benchmarking of A 4D Treatment Planning System for Scanned Ion Beam Therapy," Medical Physics, vol. 40:051722 (May 2013).
Robinson, et al., "An Evaluation of the Clarity 3D Ultrasound System for Prostate Localization," Journal of Applied Clinical Medical Physics, 13(4):100-112 (Jul. 2012).
Roujol, et al., "Characterization of Respiratory and Cardiac Motion From Electro-Anatomical Mapping Data for Improved Fusion of MRI to Left Ventricular Electrograms," PloS One, 2013, vol. 8, No. 11, p. e78852.
Saint-Gobain Ceramics & Plastics Inc: "Scintillation Materials and Assemblies, About Saint-Gobain Crystals," Saint-Gobain Crystals Handbook, 2004-2019, 12 Pages.
Sauli F., "Radiation Imaging with Gaseous Detectors," Nuclear Instruments and Methods in Physics Research A, 2018, vol. 878, pp. 1-9.
Scandurra D., et al., "Assessing the Quality of Proton PBS Treatment Delivery Using Machine Log Files: Comprehensive Analysis of Clinical Treatments Delivered at PSI Gantry 2," Physics in Medicine and Biology, vol. 61, pp. 1171-1181 (Jan. 2016).
Schardt D., et al., "Heavy-Ion Tumor Therapy: Physical and Radiobiological Benefits," Reviews of Modern Physics, vol. 82(1):383-425 (Mar. 2010).
Schlosser J., et al., "Radiolucent 4D Ultrasound Imaging: System Design and Application to Radiotherapy Guidance," IEEE Transactions on Medical Imaging, Oct. 2016, vol. 35, No. 10, pp. 2292-2300.
Shackleford J.A., et al., "On Developing B-Spline Registration Algorithms for Multi-Core Processors," Phys. Med. Biol., vol. 55, pp. 6329-6351 (Oct. 2010).
Sharma A., et al., "New Non-Invasive Therapy for Cardiac Arrhythmias using Stereotactic Radiosurgery: Initial Feasibility Testing," Heart Rythm, vol. 4(5):S68, Abstract (May 2007).
Sharma A., et al., "Non-Invasive Ablation of the Left Superior Pulmonary Vein-Left Atrial Junction Using Stereotactic Focused Radiation," Circulation, vol. 116:489, Abstract (Oct. 2007).
Sharma A., et al., "Non-Invasive Approach to Myocardial Ablation: Pathology of Stereotactic Robot Targeted High Energy X-Ray Lesions at Potential Arrhythmia Sites," Heart Rhythm, vol. 5(5): S67 (AB32-3), Abstract (May 2008).
Sharma A., et al., "Noninvasive Stereotactic Radiosurgery (CyberHeart) for Creation of Ablation Lesions in the Atrium," Heart Rhythm, 2010, vol. 7, pp. 802-810, DOI: 10.1016/j.hrthm.2010.02.010.

(56) References Cited

OTHER PUBLICATIONS

Smith, Scott, Ultrasound Miniaturization, 2011 Joint AAPM / COMP Meeting Jul. 31-Aug. 4, 2011, Vancouver, available at: https://www.aapm.org/meetings/amos2/pdf/59-17269-42515-909.pdf.

Soejima K., et al., "Catheter Ablation in Patients With Multiple and Unstable Ventricular Tachycardias after Myocardial Infarction: Short Ablation Lines Guided by Reentry Circuit Isthmuses and Sinus Rhythm Mapping," Circulation, 2001, vol. 104, pp. 664-669.

Soejima K., et al., "Endocardial and Epicardial Radiofrequency Ablation of Ventricular Tachycardia Associated With Dilated Cardiomyopathy: The Importance of Low-Voltage Scars," Journal of American College of Cardiology, 2004, vol. 43, pp. 1834-1842, DOI: 10.1016/j.acc.2004.01.029.

Solevi P., "Study of an In-Beam PET System for CNAO, the National Centre for Oncological Hadrontherapy," PHD Thesis, Milano University, 2007, pp. 1-142 (144 Pages).

Sosnovik D.E., et al., "Magnetic Nanoparticles for MR Imaging: Agents, Techniques and Cardiovascular Applications," Basic Research in Cardiology, 2008, vol. 103, No. 2, pp. 122-130.

Suleiman M., et al., "The Noncoronary Cusp as a Site for Successful Ablation of Accessory Pathways: Electrogram Characteristics in Three Cases," Journal of Cardiovascular Electrophysiology, 2010.

Takami M., et al., "Effect of Left Atrial Ablation Process and Strategy on Microemboli Formation During Irrigated Radiofrequency Catheter Ablation in an In Vivo Model," Circulation. Arrythmia and Electrophysiology, 2016, vol. 9:e003226, DOI: 10.1161/CIRCEP.115.003226.

Topolnjak, et al., "Image-Guided Radiotherapy for Left-sided Breast Cancer Patients: Geometrical Uncertainty of the Heart," International Journal of Radiation Oncology, Biology, Physics, 82(4):e647-e655 (Mar. 2012).

Uhl M., et al., "High Control Rate in Patients With Chondrosarcoma of the Skull Base After Carbon Ion Therapy: First Report of Long-Term Results," Cancer, 2014, vol. 120, pp. 1579-1585.

Van Der Ree, et al., "Cardiac Radioablation—A Systematic Review," Heart Rhythm, vol. 17(8):1381-1392 (Aug. 2020).

Watts D.A., "Detectors for Quality Assurance in Hadrontherapy," Doctoral Thesis, University of Barcelona, May 30, 2013, 265 Pages.

Wellenberg R.H.H., et al., "Metal Artifact Reduction Techniques in Musculoskeletal CT-Imaging," European Journal of Radiology, 2018, vol. 107, pp. 60-69.

Yu L., et al., "Autonomic Denervation With Magnetic Nanoparticles," Circulation, 2010, vol. 122, pp. 2653-2659.

Zei P.C., et al., "Ablative Radiotherapy as a Noninvasive Alternative to Catheter Ablation for Cardiac Arrhythmias," Current Cardiology Reports, Published Online on Jul. 27, 2017, Nov. 1, 2018, vol. 19, No. 79, pp. 1-9, XP036310567, Retrieved from URL: https://www.ncbi.nlm.nih.gov/pmc/articles/PMC5532420.

* cited by examiner

HEART ARRHYTHMIA NON-INVASIVE TREATMENT DEVICE AND METHOD

CROSS-REFERENCE TO RELATED APPLICATIONS

This application is a continuation of U.S. patent application Ser. No. 17/717,310, filed Apr. 11, 2022, now U.S. Pat. No. 11,951,327, which is a continuation of U.S. patent application Ser. No. 16/764,967, filed May 18, 2020, now U.S. Pat. No. 11,298,565, which is a national phase application under 35 U.S.C. § 371 of PCT/EP2018/081455, filed Nov. 15, 2018, which claims priority to European Patent Application Serial No. 17202164.4, filed Nov. 16, 2017, the entire contents of each of which are incorporated herein by reference.

TECHNICAL FIELD OF THE INVENTION

The present invention relates to a method and a device for treating arrhythmias. More particularly, the present invention relates to a method and a device for treating arrhythmias in a non-invasive way.

BACKGROUND

Heart arrhythmias are disruptions in the normal heartbeat. They affect more than 2% of the general population in Europe and are expected to at least double in the next 50 years as the population ages. Their occurrence is strongly linked to risks of heart attacks and strokes.

More particularly, heart arrhythmia is a problem with the rate or rhythm of the heartbeat. It means that the heart beats too quickly, too slowly, or with an irregular pattern. The heart beating faster than normal, above 100 beats per minute in adults, is called tachycardia. The heart beating too slowly, below 60 beats per minute, is called bradycardia. The most common type of arrhythmia is atrial fibrillation, which causes an irregular and fast heartbeat. Many factors can affect your heart's rhythm, such as having had a heart attack, smoking, congenital heart defects, and stress. Some substances or medicines may also cause arrhythmias.

Treatments may include medications, medical procedures such as ablation or implantation of a pacemaker or defibrillator, and surgery. Medications for a fast heart rate may include beta-blockers or agents that attempt to restore a normal heart rhythm such as procainamide. This latter group may have more significant side effects especially if taken for a long period of time. Pacemakers are often used for slow heart rates. Those with an irregular heartbeat are often treated with blood thinners to reduce the risk of complications. Those who have severe symptoms from an arrhythmia may receive urgent treatment with a controlled electric shock in the form of cardioversion or defibrillation.

Further, ablations are often used to treat arrhythmias. They consist in burning specific heart tissues with invasive tools such as catheters, to stop the conduction of the disrupted electrical signals. These invasive catheter ablation procedures are surgical interventions performed manually and the treatment efficacy varies largely from 50% to 80% according to the technology used and skill of the medical doctor. Moreover, the procedures require many hours and are at risk of serious complications like tissue perforation, vein stenosis or creation of a blood clot. The low quality of the lesion created by catheter ablation results in procedures which have to be repeated successive times, with increasing complexity for the medical staff and risk for the patient.

There is therefore a need for a method of treatment of cardiac arrhythmias via non-invasive ablation.

Charged particle beams are presently used for the treatment of tumors and occur in 20-30 sessions in successive days. These charged particle beams have the physical characteristic of depositing most of their energy in the last few millimeters of their path (so-called Bragg peak). By adjusting the beam's transverse position and energy, any target 3D volume can be precisely covered, sparing surrounding healthy tissues.

It has therefore been investigated how to provide a heart tissue ablating device and method comprising emitting beams of charged particles (mainly protons but also carbon, oxygen and helium ions) for ablating the said heart tissue.

However, since the position of the Bragg peak depends on the density of the body tissues traversed, any motion due to the patient's physiological inner movements such as respiration, heartbeat, digestion or else can result in a difference of density encountered by the incoming proton beam and therefore a different position of the Bragg peak. The precision of irradiation with charged particle beams is therefore strongly sensitive to motion of the target. This is one of the reasons why current charged particle beam treatments are mostly limited to the head, the neck, the hip region and more rarely, the trunk (pancreas, liver and lung).

There is therefore a need for a non-invasive device and a non-invasive method of treatment of cardiac arrhythmias via ablation based on charged particle beams, which can be adjusted to the body motion in real time to provide a safe and effective treatment.

SUMMARY OF THE INVENTION

The above problems are solved by the present invention.

According to a first aspect of the present invention, the treatment system is therefore composed of an accelerator and beamline, which create the required beam with given properties (intensity, position, angle and/or energy), of a control system to instruct the accelerator and beamline when to create the beam and what its required properties should be, of a patient positioning system, which comprises a robotic apparatus upon which the patient is immobilized, to position the patient and of an imaging system (based on double X-rays or Cone-beam Computer Tomography (CT)) to verify the patient positioning.

Animal trials have shown that charged particle beams can be used to ablate heart tissue. However, in order to ensure a safe, effective and fast procedure, the system of the present invention is able to monitor in real-time the motion of the patient inner tissues, to infer the motion of the treatment target and to adapt in consequence the beam delivery based on a pre-established motion model. The motion model informs about the allowed target position for some defined motion phases (one or more), which correspond to a combination of phases of the respiratory and cardiac cycles. This can involve 'gating' the beam when the position detected by the imaging system of the target is not as expected from the motion model for that given motion phase and cannot be compensated by the irradiation system, and 'tracking', i.e. adapting the beam transverse and longitudinal characteristics based on the identified motion phase.

Advantageously, the system is composed of a hardware and a software part. The imaging is performed fully non-invasively, i.e. it does not require to implant fiducial markers or to insert the imaging system inside the body cavities, and shall not be placed in the path of the charged particle beams.

In this regard, one or more ultrasound imaging systems are placed externally on the patient body in order to image the heart region from the abdominal or thoracic viewing windows. Imaging can be performed using one or more linear arrays, phased arrays, multi-plane arrays (also called T-shaped or X-plane) and matrix arrays ultrasound transducers to acquire 2D or 3D images at frame rates higher than the heartbeat.

These devices are used to simultaneously image parts of the heart. By knowing the position of each imaging system inside the treatment room (using for example optical markers on each imaging device and optical cameras, or magnetic sensors), one can relate the position of an object in the image to its position in 3D space. Possibly coupled with respiratory and cardiac motion sensors, this allows to detect the phase of the motion of the target and its displacement from the nominal position, which is defined in the planning.

Planning relies on performing 4D-CT (time-resolved computed tomography) scans (possibly with respiratory and cardiac sensors) to determine for one or more phases of respiratory and cardiac cycles the target for the ablation and the required beam properties (angle, energy, position, intensity) to effectively irradiate the target while sparing sensitive surrounding healthy tissues. The CTs are taken for different phases of the respiratory and cardiac cycles, in order to determine the motion of the target during respiratory and cardiac cycles. Based on this information, boundaries around the clinical target volume(s) are defined and together constitute the 'nominal' target positions. Simultaneously or at a separate time, the ultrasound imaging system (and possibly an MR system) records images of either the target regions themselves or near-by tissues for all cardiac and respiratory phases. These are used to determine a motion model: the model consists in a set of points (so-called fiducials) in ultrasound images and for each fiducial, their nominal position in space. The fiducial positions depend on the respiratory and cardiac phase and can be directly univocally correlated to the position of the ablation target. For easy visualization, the ultrasound images (and possibly MR images) can be fused to the 4D-CT images for easy identification of the structures for the medical operator.

The device and the system of the invention are convenient for the patient since they consist in a non-invasive procedure lasting less than two hours without anesthesia in a single or at worst few out-patient sessions. The invention is effective since the deep ablation of both inner and outer cardiac muscle tissue consists in continuous 3D volumes instead of the ablation points/lines performed by today's technology. Finally, they provide a risk reduction because there is no risk of infection due to surgery and do not result in the deposition of large doses to healthy tissues, contrary to ablation with X-ray/Gamma-ray/Photon beams (typically used in so-called conventional radiotherapy for the treatment of tumors).

BRIEF DESCRIPTION OF THE DRAWINGS

Further particular advantages and features of the invention will become more apparent from the following non-limitative description of at least one embodiment of the invention which will refer to the accompanying drawings, wherein.

DETAILED DESCRIPTION OF THE INVENTION

The present detailed description is intended to illustrate the invention in a non-limitative manner since any feature of an embodiment may be combined with any other feature of a different embodiment in an advantageous manner.

In the following description several terms are used in a specific way which are defined below:

The expression 'treatment/irradiation plan' refers to the patient-specific list of treatment properties (treatment room, type and position of the patient positioning system, beam species, irradiation angle, beam size, beam position, beam energy, beam intensity, number of treatment sessions, among others) in order to irradiate the appropriate volume in the patient body with the required therapeutic radiation dose. These properties are computed based on the planning CT (static or time-resolved), where the medical staff has defined the clinical target which should receive a given dose, the critical healthy tissues that should be irradiated in the least possible fashion and the margins around the clinical target that consider the possible errors related to patient positioning and motion during the delivery.

The term 'gating' refers to sending a binary signal (optical, electrical, among others) to the beam delivery system to either: pause the irradiation or resume the irradiation as planned.

The term 'tracking' refers to sending a signal to the beam delivery system to modify the irradiation beam properties (transverse size, longitudinal size, transverse position, energy, intensity, among others) in order to match the recorded motion of the irradiation target.

The term 'reference structures' refers to segmented elements (point, open line, closed line, volume) from the ultrasound images taken at planning stage, whose position in all motion phases is computed and compared (for each motion phase) to the position of the irradiation target structure in the planning CT images.

The term 'fiducials' refers to a sub-set of the 'reference structures' characterized by the fact that their motion can be univocally correlated to the motion of the irradiation target in the planning CT images, as is the case if the difference in position between the fiducial in the ultrasound image and the irradiation target in the planning CT image is constant for all motion phases.

The expression 'nominal positions' refers to the position of the fiducial(s) established in the planning phase. This is univocally also correlated to the position of the target in the planning CT.

The expression 'motion boundaries' refers to margins taken around the clinical target volume to account for allowed motion. These depend on the critical surrounding healthy tissues and on how the motion is modelled and mitigated. For example, a possible approach is to consider only one phase of the respiratory and cardiac cycles and take large margins for the allowed motion, in order to have a large gating window. Another approach is to consider many phases of the respiratory and cardiac cycles and take small margins for the allowed motion, in order to track the motion and limit the irradiation of healthy tissues surrounding the clinical target.

The expression 'respiratory and cardiac sensors' refers to any (optical, electrical, magnetic, acoustic, among others)

means to infer the present respiratory cycle phase and cardiac cycle phase. This includes also a simple time counter, which in a predictive manner can determine which is the current phase of the respiratory and cardiac cycles based on established regular patterns for the specific patient.

Figure 1:
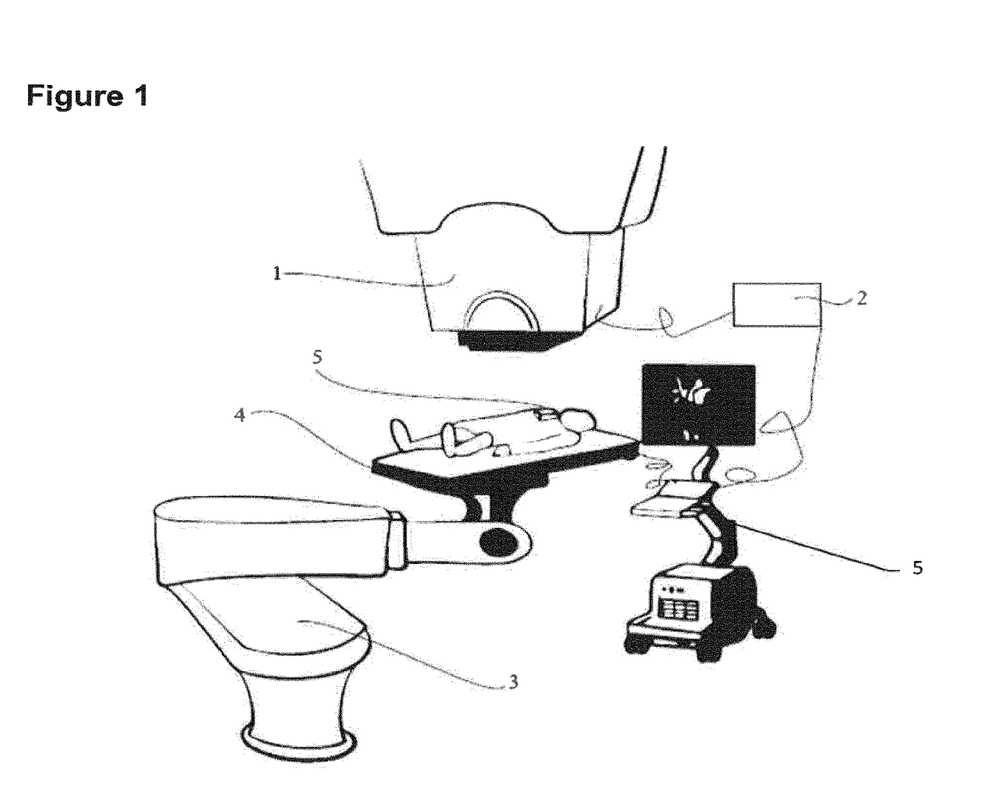
FIG. 1 represents a heart arrhythmia treatment device according to a preferred embodiment of the present invention.

The ablating device of the present invention is composed of a charged particle emitting system 1, which preferably comprises an accelerator, and a beamline, which create the required beam with a given intensity, position, angle and energy.

It further comprises a control system 2 for instructing the accelerator and beamline when to create the beam and what its required properties should be.

It also comprises a patient positioning system 3, which comprises a robotic apparatus 4 to position the patient and an imaging system (based on double X-rays or Cone-beam CT) to verify the patient positioning.

In addition to this, to be able to track the target motion, the ablating device further comprises an ultrasound cardiac imaging system 5 including a probe, connected to a movable tray with hardware control and signal processing units and a CPU, preferably with a screen (possibly combined with ECG (electrocardiogram) and respiration monitoring).

The control system 2 is then regulated by the results of the ultrasound imaging systems 5 during the treatment.

Of course, other additional modalities are also possible: MRI, ECGI, among others.

Ablation Process

The ablation process is as follows.

Figure 2:
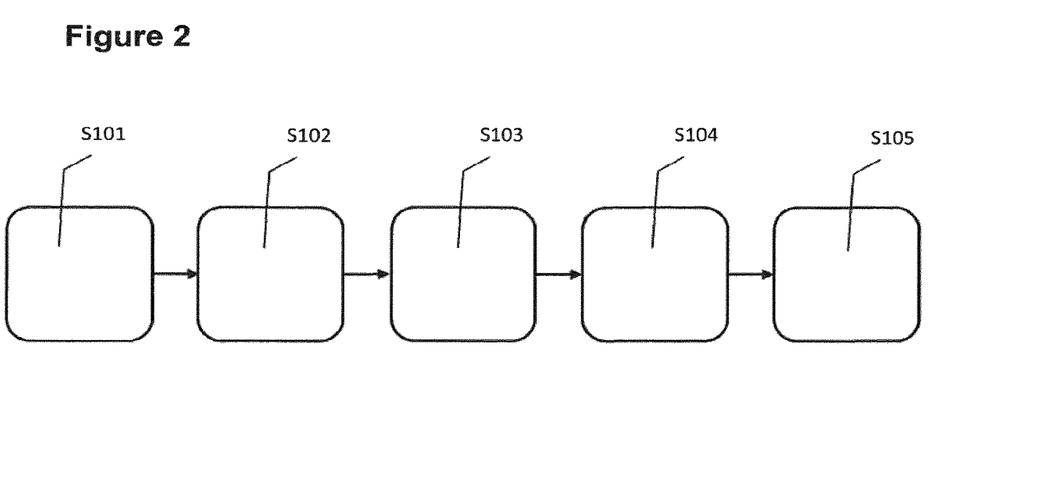
FIG. 2 schematically represents heart arrhythmia treatment method according to a preferred embodiment of the present invention.

First, a treatment plan is defined. That is, the 3D target volume (~2-200 cm$^3$), the target motion, the therapeutic dose (~20-60 Gy), the irradiation angle(s) and critical tissues and their dose limits have to be calculated and defined. The treatment plan is performed for one or more respiratory and cardiac cycle phases. For each of these, the treatment plan includes an irradiation plan for the clinical target position and its allowed motion boundaries, within which the treatment can be considered safe.

More particularly, this planning step S101 comprises first taking ultrasound and CT images of the heart either simultaneously or one after the other for all cardiac and respiratory cycles, contouring by a medical staff of the target region in CT images for one or more motion phases (a motion phase can combine various respiratory and cardiac cycle phases), determining the beam irradiation parameters for each of the chosen motion phases based on the target region and surrounding healthy tissues, determining, for each of the chosen motion phases, boundaries for the target region outside of which irradiation should be stopped because it is unsafe. Successively, planning consists in performing an image segmentation on ultrasound images, co-registering/fusing the ultrasound images with MRI or CT images where the target region appears, selecting one or more fiducials (from all the automatically segmented reference points/lines in the ultrasound frames based on their stability of relative position with respect to the target regions for all defined motion phases), and recognizing the corresponding positions of the fiducials in all the other data frames of the ultrasound images.

On the treatment day, a patient positioning step S102 is carried out where a patient is positioned in the treatment room via immobilization devices on a treatment table/chair. The table/chair is robotized in order to hold a specific position and to, on command, perform translations and/or rotations in space.

Then, once the patient is positioned, a patient position verification step S103 is carried out where the patient position is verified through embarked in-room Computer Tomography (CT) or double X-ray imaging. If the position is different from the expected one, the patient position is modified using the robotized table/chair. A re-verification of the patient position may be performed.

The previous steps are repeated iteratively until it is verified that the patient position is the same as when the CT imaging (of the previous planning step) took place. Once the patient position is verified and judged correct, the irradiation S104 starts: a single irradiation is emitted at prescribed angle of prescribed volume of the heart (as determined during treatment planning) together with non-invasive imaging via an ultrasound system consisting of one or multiple ultrasound transducers placed out of the irradiation field, possibly combined with cardiac and respiratory cycle sensors.

Then a judgment step S105 is carried out, where based on the imaging, the target position is determined in real-time, the relevant motion phase is identified and the target position is compared to its nominal position and its motion boundaries.

More particularly, based on the imaging, and possibly aided by cardiac (ECG) and respiratory (monitoring of abdomen movement for example) cycle monitoring, the system recognizes the relevant motion phase of the 4D-CT and thus the relevant irradiation plan for that phase. It should be understood of course that in the case that the treatment plan is done for only one motion phase, the loading of the irradiation plan does not correspond to any change in the control system 2 since there is, in such case, no irradiation plan choice as single one is available. This is achieved through image segmentation and registration on ultrasound images to determine the position of the fiducials (reference points/lines) on the ultrasound images and thus to derive from them the relevant irradiation plan. The system then sends this information to the control system 2 to set up the machine for irradiation with the correct beam parameters. The system also compares the determined fiducial positions to the nominal positions for safe irradiation for that particular irradiation plan and finally, in case the difference in position is smaller than the pre-established margin, it sends a gating signal to the control system 2 to allow irradiation or in case the difference in position is larger than the pre-established margin, sends a gating signal to the control system 2 to pause the irradiation.

In other words, based on the imaging, the beam target position is determined in real-time and compared to an expected position according to a motion model defined in the treatment planning. If the beam target position is outside of pre-established boundaries, the beam irradiation is gated (paused). If the position is within the boundaries (for example within a sphere of 1 mm radius from the nominal position of a particular fiducial point), irradiation is allowed and the beam characteristics correspond to those of a pre-established treatment plan. A safety system is integrated which stops irradiation if movement is outside of given boundaries (for example, when the motion of the earlier given fiducial point is larger than 1 mm from the nominal position).

As explained above, the irradiation system comprises an accelerator and a beamline to provide the beam of accelerated charged particles of the correct properties (size, intensity, energy, position). The beamline can be mounted on a rotating mechanical frame (gantry) to change the angle of irradiation. All beam properties are controlled by the control system 2 based on the off-line planned treatment and motion model and on the on-line monitoring of both the beam position and intensity and the target motion.

In the case of irradiation with multiple angles, when irradiation is completed for one gantry angle, irradiation is stopped and the gantry is rotated to the new pre-determined angle. If needed, the patient positioning and position verification step are performed. Then, the irradiation step is performed for this new angle.

The imaging system and process will now be explained more in details.

Ultrasound Tracking System and Method

The ultrasound system of the present invention is preferably composed of one or multiple 2D or 3D ultrasound transducers for continuous visualization of the heart transabdominally/thoracically, i.e. between ribs and/or through liver for all time frames (10-30 Hz). Positioning and tuning of the devices can be made by an operator but a holding system shall enable to fix the position for long continuous acquisition times, e.g. about 1 to 2 hours, with only remote supervision and/or control.

The transducer(s) and/or its support system have optical or magnetic markers so as to be able to geolocalize and continuously monitor their position in the treatment/imaging room coordinate frame and to fuse/co-register their image to CT and MR images. Thus, the transducer position in space can be measured and tracked in order to associate the registered fiducials with the corresponding structure in the CT or MR image. The ultrasound imaging system is such that it can withstand operation with radiation exposure (indirect emission of neutrons and gamma rays from the incoming treatment beam). Alternatively, in case the data processing cannot be put in the treatment/imaging room, the signal can be transported with negligible loss towards a nearby area via analogic or digital data transmission cables.

The ultrasound system can be co-adjuvated by monitoring systems for the cardiac (ECG) and respiratory cycles (optical abdomen motion monitoring for example).

In the case of atrial fibrillation, the target region for ablation is typically around the pulmonary veins at their intersection with the left atrium. The ultrasound-based tracking system could thus aim at visualizing the left atrium and the pulmonary veins. The atrium wall could be used to quantify the motion of the pulmonary veins and/or Doppler ultrasound imaging could be used to image the blood flow and thus indirectly determine the position of the veins. In the case of ventricular tachycardia, the target region for ablation could be determined by late gadolinium enhanced MRI and/or electrophysiological mapping using mapping catheters and/or electrocardiographic imaging (ECGI). The ultrasound-based tracking system would thus aim at visualizing for example the ventricular outer wall and/or the ventricular septum.

A first, offline, computer program runs before the ablation treatment and enables to automatically segment the ultrasound images, discard some structures based on user-given criteria keeping only 'reference' structures and co-register/fuse the reference structures to the CT images for one of the respiratory and cardiac motion phases used for the treatment planning. The computer program then performs an image segmentation and registration for all the other motion phases to establish the new position of the reference structures and co-registers/fuses the position of the structures to the CT images for the same motion phase. The computer then determines the structure(s) whose position relative to the irradiation target region in the CT images is the most stable for all motion phases. These are thus 'fiducials' for the target motion. The operator defines or loads the motion boundaries around the clinical target region in the CT and the computer computes the corresponding position margins for the fiducials in the ultrasound image. The same process is repeated for all the cardiac and respiratory phases used for the treatment planning.

A second, online, computer program runs during the ablation treatment and based on the input from the first computer program, searches via automatic image segmentation and registration for the position of the fiducials on the live ultrasound images. Based on this information and possibly also on the information from cardiac and respiratory motion sensors, the computer determines which cardiac and respiratory cycle phase is relevant and sends the information to the control system 2, which, if it is not already loaded, loads the corresponding irradiation plan. The computer then co-registers/fuses the position of the fiducials to those in the irradiation plan, where the target region and the safe motion boundaries are given. If the position compared to the target region is inside the safety margin, the system sends a command to the control system 2 to enable the irradiation. On the other hand, if the position compared to the target region is larger than the safety margin, the computer program sends a 'stop irradiation' to the control system 2.

While the embodiments have been described in conjunction with a number of embodiments, it is evident that many alternatives, modifications and variations would be or are apparent to those of ordinary skill in the applicable arts. Accordingly, this disclosure is intended to embrace all such alternatives, modifications, equivalents and variations that are within the scope of this disclosure. This for example particularly the case regarding the different apparatuses, which can be used.

What is claimed is:

1. A system for use with a radiation therapy system that generates a charged particle beam to ablate targeted tissue of a heart of a patient for non-invasive treatment of heart arrhythmia, the system comprising:
   an ultrasound cardiac imaging system configured to image a region of the heart to assess motion of the targeted tissue and corresponding cardiac and respiratory cycle phases of the patient; and
   a control system configured to process an irradiation plan comprising positional information of the targeted tissue imaged during a planning stage, the control system further configured to, during a treatment stage, process ultrasound images acquired with the ultrasound cardiac imaging system and instruct the radiation therapy system to generate the charged particle beam in accordance with the irradiation plan to ablate the targeted tissue of the heart based on information of the cardiac and respiratory cycle phases provided by the ultrasound cardiac imaging system during the treatment stage.

2. The system of claim 1, wherein the control system is configured to, during the treatment stage, determine the irradiation plan for a corresponding cardiac and respiratory cycle phase.

3. The system of claim 1, wherein the control system is configured to determine the positional information of the targeted tissue imaged during the planning stage by a Computer Tomography (CT) system or a magnetic resonance imaging (MRI) system.

4. The system of claim 1, wherein the control system is configured to identify positional differences between the acquired ultrasound images at the treatment stage and the images of the targeted tissue at the planning stage.

5. The system of claim 4, wherein, if the positional differences are determined to be within established safety margins according to the irradiation plan, the control system is configured to permit irradiation of the targeted tissue with the charged particle beam to ablate the targeted tissue.

6. The system of claim 4, wherein, at the planning stage, the control unit is configured to determine fiducials of the targeted tissue.

7. The system of claim 6, wherein the control system is configured to determine a change in position of the targeted tissue based on differences in positions of the fiducials in the acquired ultrasound cardiac images.

8. The system of claim 1, wherein the control system is configured to cause the radiation therapy system to deliver a Bragg peak of the charged particle beam to the targeted tissue.

9. The system of claim 1, wherein the ultrasound cardiac imaging system comprises an ultrasound transducer having a marker coupled thereto.

10. The system of claim 9, wherein the marker comprises an optical marker or a magnetic marker.

11. The system of claim 9, further comprising a cardiac motion sensor or a respiratory motion sensor or both for use with the marker.

12. The system of claim 1, further comprising a cardiac cycle monitor configured to work in combination with the ultrasound cardiac imaging system.

13. The system of claim 12, wherein the cardiac cycle monitor comprises an electrocardiogram (ECG) monitoring device.

14. The system of claim 1, further comprising a respiratory cycle monitor configured to work in combination with the ultrasound cardiac imaging system.

15. The system of claim 14, wherein the respiratory cycle monitor is configured to monitor abdomen movement of the patient.

16. The system of claim 1, further comprising a cardiac cycle monitor and a respiratory cycle monitor, both of which are configured to work in combination with the ultrasound cardiac imaging system.

17. The system of claim 1, wherein the control system is configured to cause the radiation therapy system to generate the charged particle beam at a specified intensity, position, angle, and energy.

18. A method for non-invasive treatment of heart arrhythmia using a radiation therapy system that generates a charged particle beam to ablate targeted tissue of a heart of a patient, the method comprising:
   imaging a region of the heart using an ultrasound cardiac imaging system to assess motion of the targeted tissue and corresponding cardiac and respiratory cycle phases of the patient;
   processing an irradiation plan comprising positional information of the targeted tissue imaged during a planning stage;
   processing ultrasound images acquired with the ultrasound cardiac imaging system during a treatment stage; and
   instructing the radiation therapy system to generate the charged particle beam in accordance with the irradiation plan to ablate the targeted tissue of the heart based on information of the cardiac and respiratory cycle phases provided by the ultrasound cardiac imaging system during the treatment stage.

19. The method of claim 18, wherein the targeted tissue is imaged during the planning stage by a Computer Tomography (CT) system.

20. The method of claim 18, further comprising identifying positional differences between the acquired ultrasound images at the treatment stage and the images of the targeted tissue at the planning stage,
   wherein, if the positional differences are determined to be within established safety margins according to the irradiation plan, instructing the radiation therapy system comprises permitting irradiation of the targeted tissue with the charged particle beam for ablating the targeted tissue.

* * * * *